(12) United States Patent
Yoo et al.

(10) Patent No.: US 11,185,304 B2
(45) Date of Patent: Nov. 30, 2021

(54) SYSTEMS AND METHOD FOR ACOUSTIC POWER SCALABLE CHARGE-REDISTRIBUTION ULTRASONIC SYSTEM WITH ON-CHIP ABERRATION COMPENSATION FOR PORTABLE ULTRASONIC APPLICATIONS

(71) Applicant: Khalifa University of Science and Technology, Abu Dhabi (AE)

(72) Inventors: Jerald Yoo, Abu Dhabi (AE); Judyta B. Tillak, Abu Dhabi (AE)

(73) Assignee: KHALIFA UNIVERSITY OF SCIENCE AND TECHNOLOGY, Abu Dhabi (AE)

( * ) Notice: Subject to any disclaimer, the term of this patent is extended or adjusted under 35 U.S.C. 154(b) by 779 days.

(21) Appl. No.: 15/802,772

(22) Filed: Nov. 3, 2017

(65) Prior Publication Data

US 2018/0116632 A1    May 3, 2018

Related U.S. Application Data

(60) Provisional application No. 62/416,967, filed on Nov. 3, 2016.

(51) Int. Cl.
  *A61B 8/14*     (2006.01)
  *B06B 1/02*     (2006.01)
  (Continued)

(52) U.S. Cl.
  CPC .......... *A61B 8/145* (2013.01); *A61B 8/4488* (2013.01); *A61B 8/4494* (2013.01); *B06B 1/0215* (2013.01); *B06B 1/0292* (2013.01); *B06B 1/0607* (2013.01); *G01N 29/0654* (2013.01); *G01N 29/2406* (2013.01); *G01N 29/2437* (2013.01); *G01N 29/34* (2013.01);
  (Continued)

(58) Field of Classification Search
  None
  See application file for complete search history.

(56) References Cited

U.S. PATENT DOCUMENTS 5,638,013 A  *  6/1997  Iwata ............... G11C 5/145
                                             327/126
2005/0124884 A1*  6/2005  Bolorforosh ......... A61B 8/4488
                                             600/439
(Continued)

OTHER PUBLICATIONS

Judyta Tillak, et al., A 2.34μj/Scan Acoustic Power Scalable Charge-Redistribution pMUT Interface System with On-Chip Aberration Compensation for Portable Ultrasonic Applications, IEEE Asian Solid-State Circuits Conference, Nov. 5, 2016, 4 pages.

*Primary Examiner* — Katherine L Fernandez
(74) *Attorney, Agent, or Firm* — Billion & Armitage

(57) ABSTRACT

The present disclosure is generally directed to an ultrasonic transducer interface system for use within portable 2-D ultrasonic imagers and includes an on-chip adaptive beamformer and Charge-Redistribution TX (CR-TX) to provide a drive strength of up to 500 pF/channel at 5 MHz (or 10 nF at 250 kHz) while reducing the TX drive power by at least 30% compared to other ultrasonic transducer TX drivers. The ultrasonic transducer interface system can be implemented in a single chip via, for example, a complementary metal oxide semiconductor (CMOS) process.

15 Claims, 9 Drawing Sheets

(51) Int. Cl.
  *B06B 1/06* (2006.01)
  *G01N 29/24* (2006.01)
  *G01N 29/44* (2006.01)
  *A61B 8/00* (2006.01)
  *G01S 7/52* (2006.01)
  *G01S 15/89* (2006.01)
  *G01N 29/06* (2006.01)
  *G01N 29/34* (2006.01)

(52) U.S. Cl.
  CPC ........ *G01N 29/4463* (2013.01); *G01S 7/5208* (2013.01); *G01S 7/52047* (2013.01); *G01S 7/52049* (2013.01); *G01S 15/8915* (2013.01); *A61B 8/4427* (2013.01); *A61B 8/56* (2013.01); *A61B 8/58* (2013.01)

(56) References Cited

U.S. PATENT DOCUMENTS

2009/0299192 A1* 12/2009 Asafusa ............... A61B 8/4483
                                                              600/459
2013/0345566 A1* 12/2013 Weitzel ................ A61B 8/488
                                                              600/445
2015/0157299 A1*  6/2015 Hopple .................... A61B 8/58
                                                              600/459
2018/0246193 A1*  8/2018 Kline ................... B06B 1/0215

* cited by examiner

|  | 1 | 2 | 3 | 4 | 10 |
|---|---|---|---|---|---|
| Transducer | CMUT | PMUT | PMUT | CMUT | PMUT |
| Application | Imaging | Rangefinder | Medical diagnosis | Imaging | diagnosis |
| Medium | biomed | air | biomed | biomed | adaptive (5 media) |
| Max. TX Frequency | 10MHz | 250MHz | 40MHz | 5.2MHz | 100kHz-5Mhz |
| Scan Depth | 100mm | 1m | 100mm | x | 100mm |
| TX Voltage | 60V | 32V | 32V | 30V | 6V |
| Medium Adaptive | x | x | x | x | o |
| Scalability | o | x | x | x | o |
| Technology | 1.5μm | 0.18μm | 0.13μm | 0.18μm | 65nm |
| # of Channels | 32 x 32 | 10 | 7 | 4 | 8-scalable |
| Operation Freq.* | 5MHz | 220kHz | 8MHz | 3.3MHz | 250kHz |
| LOAD/ch | 2.5pF | 10pF | 17pF | 40pF | 500pF |
| Energy/Scan | 72μJ** | 13μJ | 2.6μJ | 8.58μJ** | 2.34μJ |
| * The frequency used to report the Energy/Scan ** Estimated based on max. fram rate | | | | | |

FIG. 3

(FIG. 6a)  NO Voltage  (FIG. 6c)
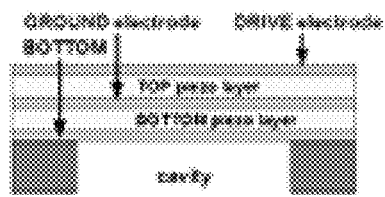
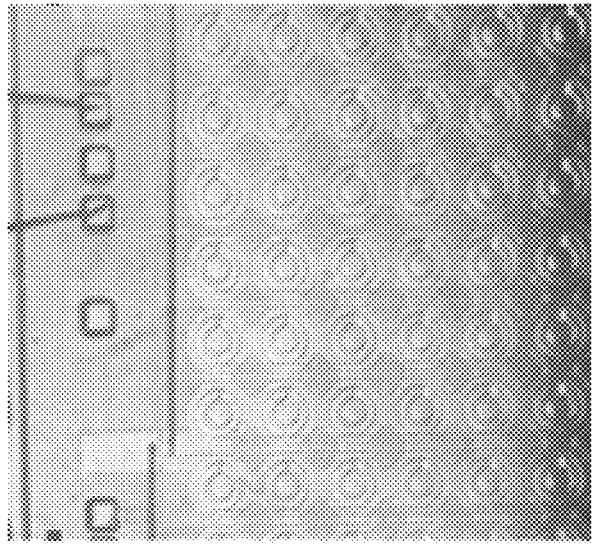
(FIG. 6b) 5V Applied to the DRIVE electrode
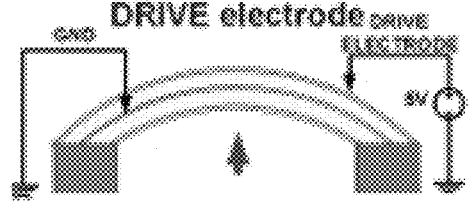

SYSTEMS AND METHOD FOR ACOUSTIC POWER SCALABLE CHARGE-REDISTRIBUTION ULTRASONIC SYSTEM WITH ON-CHIP ABERRATION COMPENSATION FOR PORTABLE ULTRASONIC APPLICATIONS

CROSS-REFERENCE TO RELATED APPLICATIONS

The present non-provisional application claims the benefit of U.S. Provisional Patent Application Ser. No. 62/416,967 filed on Nov. 3, 2016, the entire content of which is hereby incorporated by reference.

TECHNICAL FIELD

The present disclosure generally relates to portable ultrasonic imaging devices, and more particularly, to acoustic power scalable charge-redistribution ultrasonic transducer interfaces with on-chip aberration compensation.

BACKGROUND INFORMATION

In portable Ultrasonic Imaging Systems (UIS), chip area reduction remains an important goal as transducer arrays can contain up to thousands of elements which each require a separate frontend. Long distance scans and high frequency (e.g., >5 MHz) imaging require high acoustic power by using large capacitance acoustic piezoelectric Micromachined Ultrasonic Transducers (pMUTs), using multi-element transmission channels, or applying High Voltage (HV) driving to the transducers. For biomedical imagers, the transmitter pulsar (TX) drivers may consume as much as 90% of total system power. As a result, reducing the TX power without a significant loss of acoustic pressure raises numerous non-trivial challenges.

UIS devices also require fast and effective beamformer capable of driving ultrasonic transducers in different media. For example, pMUT micromachining allows fabrication of μ-scale acoustic membranes where the physical matching of the channels plays a significant role. Mismatch in signal power, element spacing, and non-homogenous media can result in aberration and may deteriorate the image quality.

BRIEF DESCRIPTION OF THE DRAWINGS

These and other features and advantages will be better understood by reading the following detailed description, taken together with the drawings wherein:

FIG. 3 is a table comparing characteristics of one embodiment of a system consistent with the present disclosure with four other systems/methods.

FIGS. 6A-6B generally illustrate a ultrasonic transducer structure and modes of operation.

FIG. 6C generally illustrates one embodiment of a micrograph of pMUT bimorph array suitable for use in the system of FIG. 1.

DETAILED DESCRIPTION

The present disclosure is generally directed to an ultrasonic transducer interface system for use within 2-D ultrasonic imagers and includes an on-chip adaptive beamformer and Charge-Redistribution TX (CR-TX) circuits to provide a drive strength of up to 500 pF per channel at 5 MHz, or 10 nF at 250 kHz when driving a given channel with 4 CR-TX circuits, while reducing the TX drive power by at least 30% compared to other ultrasonic transducer TX drivers. The ultrasonic transducer interface system can be implemented in an application-specific integrated circuit (ASIC) using, for example, a complementary metal oxide semiconductor (CMOS) process.

Figure 1A:
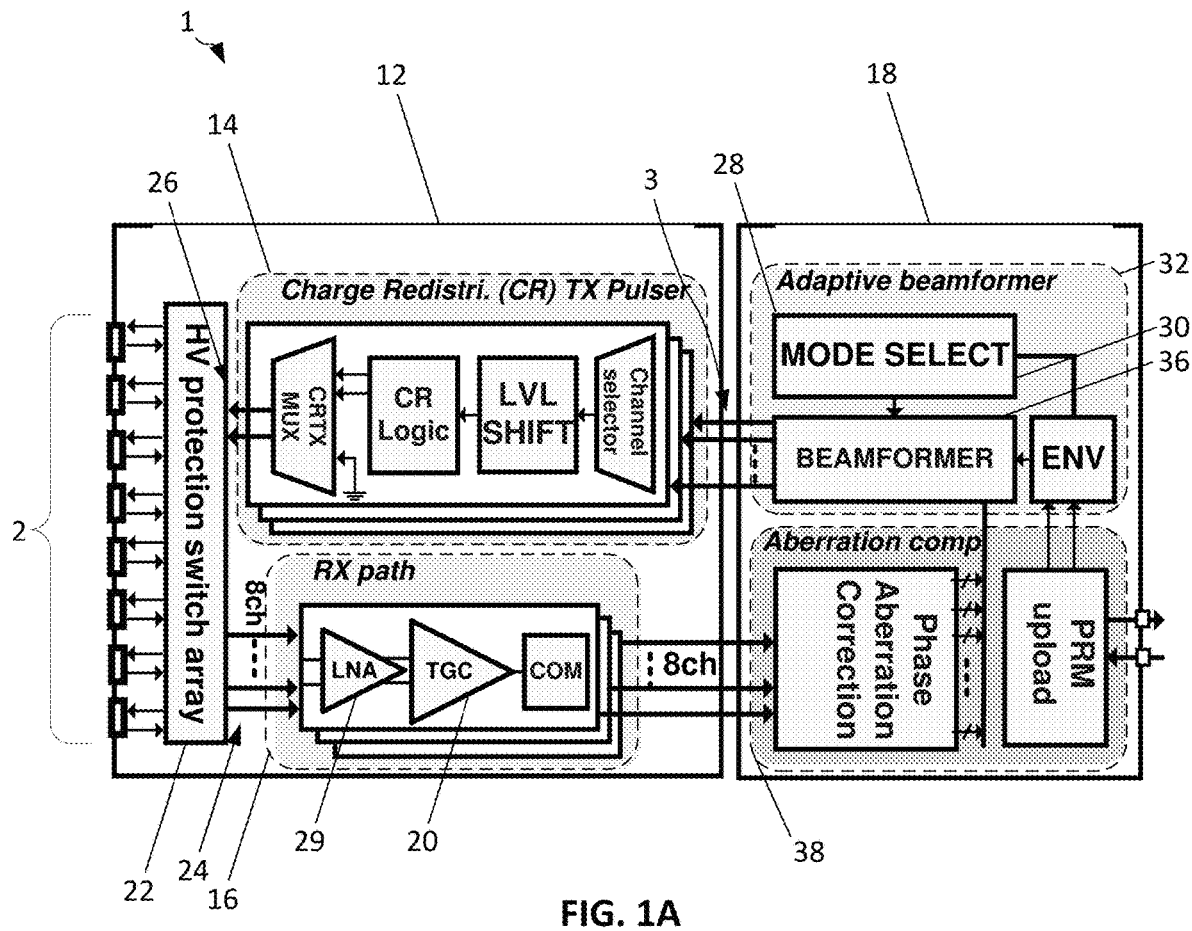
FIG. 1A is a block diagram showing the architecture of one embodiment of a system consistent with the present disclosure.

Turning to the figures, FIG. 1A shows a block diagram generally illustrating one embodiment of an ultrasonic transducer interface system 1. The system 1 may be implemented as a single chip. For instance, the system 1 may be implemented as a complementary metal oxide semiconductor (CMOS) ASIC chip using known photolithography techniques. However, this disclosure is not necessarily limited in this regard and the system 1 may be implemented via multiple chips.

In an embodiment, the system 1 comprises a multi-channel analog front end (AFE) 12 and a digital back-end (DBE) 18. The AFE 12 includes a transmit (TX) path in the form of one or more charge redistribution transmit pulser (CR-TX) circuits, which will be discussed in greater detail below. The AFE 12 includes a receive (RX) path 16, with receive path 16 having a plurality of RX channel circuits. Each of the RX channel circuits include a low noise amplifier (LNA) 29, and a digitally controlled Time-Gain Compensation (TGC) amplifier 22. However, the components of the receive path 16 are application specific and are not intended to be limited to the embodiment shown in FIG. 1A.

As further shown, the AFE 12 further includes a plurality of ultrasonic transducer channels 2. As shown, the ultrasonic transducer channels may be implemented as a phased-array having from one to eight (1 to 8)-channels, with element separation of 250 μm-5 mm (for 8-ch mode), or 1.5 cm (for 4- or 2-ch mode). In other embodiments, the phased-array may have more than 8 channels, depending on a desired application. The phased-array may be formed as an M×N array of ultrasonic transducer elements (see FIG. 6C). Therefore, each of the ultrasonic transducer channels may comprise N number of elements in the phased-array. In this example, each row of the M×N array may form a single, independently-drivable ultrasonic transducer channel.

In any event, and in accordance with an embodiment, each of the ultrasonic transducer elements forming the phased-array may comprise, for example, Piezoelectric Micromachined Ultrasonic Transducers (pMUTs), Capacitive Micromachined Ultrasonic Transducers (cMUTs), bulk piezoelectric transducers, or any other ultrasonic transducer device capable of receiving an electrical signal and converting them same into mechanical energy, i.e., sound. However, it should be noted that embodiments herein may be equally applicable to other known ultrasonic transducer types, and this disclosure should not be construed as limited in this regard.

The AFE 12 may further include digitally controlled High Voltage (HV) switch array 22. The HV switch array 22 may be used to shield the Low Voltage (LV) RX path/bus 24 from HV TX path/bus 26. As discussed below, the HV switch array 22 may include a switching arrangement per TX pulser that reduce power consumption during TX sequences (see FIG. 7A).

Continuing on, the DBE 18 includes and adaptive beamformer 32 and an aberration compensation circuit 38. Note, while the DBE 18 and the beamformer 32 are shown as separate elements, this disclosure is not necessarily limited in this regard. For instance, the DBE 18 and the beamformer 32 may be formed as a single chip. The DBE 18 may also be referred to as a beamformer controller 18.

As discussed further below with reference to FIG. 1B, the adaptive beamformer 32 may be configured to dynamically focus and/or adjust beam direction during operation to accommodate varying types of mediums. In an embodiment, the DBE 18 supports a plurality of different medium types. For example, the DBE 18 may support five (5) different medium types such as air (343 m/s), rubber (926 m/s), alcohol (1143 m/s), water (1493 m/s) and bio-material (1533 m/s). The difference in acoustic speed in various media requires using different corresponding parameters and unit delays. The DBE 18 may therefore store parameters and unit delays associated with each supported medium type in a high-speed memory, e.g., lookup table (LUT) 42 of FIG. 1B. Therefore, the DBE 18 may adjust resolution relative to a selected medium in a dynamic, real-time manner, e.g., within 1-100 clock cycles.

The DBE 18 includes pulse-to-echo sequencer (P2E) 28 to transition between transmitting pulses and receiving corresponding echoes. The DBE 18 further includes Beam-Steering (BS) logic 34, which may be utilized for keeping the RX path 16 closed/disabled during, for instance, use in therapeutic applications whereby only the TX path 14 is utilized.

In an embodiment, the P2E sequencer 28 of the adaptive beamformer 32 is designed to scan the environment in front of the array of channels 2 with +30°/−30° field and depth from −2.5 to 10 cm using 1 TX driver per channel. The same medium can also be scanned with 2 or 4, or N number of TX drivers per channel if more acoustic power is needed, or the load is significantly large. By adjusting the number of TX drivers (e.g., CR-TX pulser circuits 14) per channel (that operate simultaneously), the system 1 can drive a 100× larger load (500 pF) per channel than other known systems at the desired frequency with a full swing of output TX voltage.

During operation, the adaptive beamformer 32, and more specifically beamformer sequencer 36, may output one or more driving signals 3 based on a selected medium type. The one or more driving signals 3 may comprise pulse-width modulated (PWM) signals. Each of the CR-TX pulser circuits 14 may receive the driving signals 3 to cause one or more of the ultrasonic channels 2 to output ultrasonic sound energy.

In an embodiment, the AFE 12 may have an operational bandwidth from 100 kHz to 5 MHz, and a maximum gain of 60 dB to enable deep tissue scans (~100 mm) in high attenuation media, e.g., intracranial imaging. Note, the low cut off frequency of 100 kHz may be selected to target imaging application and corresponds to $\lambda/2=1.7$ mm in air.

Figure 1B:
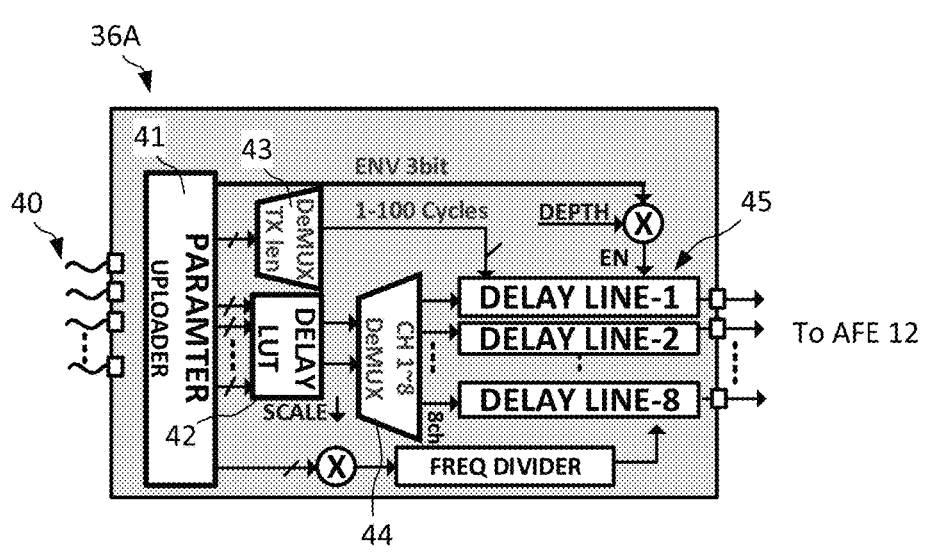
FIG. 1B is a block diagram showing the architecture of a beamformer sequencer in accordance with an embodiment of the present disclosure.

FIG. 1B shows an example architecture of a beamformer sequencer 36A consistent with an embodiment of the present disclosure. The beamformer sequencer 36A may be suitable for use as the beamformer sequencer 36 of FIG. 1A.

As shown, the beamformer sequencer 36A includes a parameter uploader 41 includes input lines/terminals 40 to, for example, receive input signals (e.g., digital logic via a bus) for reprogramming purposes, e.g., to adjust/add medium parameters. The parameter uploader 41 may access a delay lookup table (LUT) 43, to retrieve parameters associated with a selected medium, e.g., the medium to be imaged such as bio-material. The LUT 43 may include a plurality of predefined pulse patterns, with each predefined pulse pattern being associated with a predefined medium type. Each predefined pulse pattern may include the number of pulses to emit during each transmit cycle, duration of each pulses, the number of channels to utilize, and channel delays for each channel.

Thus, the LUT 42 may be accessed and a lookup may be performed based on a selected media type. Once located, parameters including a predetermined pulse output pattern and TX delay length for each channel may be retrieved. The TX delay length 43 may then be used in combination with the predetermined pulse pattern to output digital driving signals, e.g., PWM signals, via delay lines 45.

Figure 2:
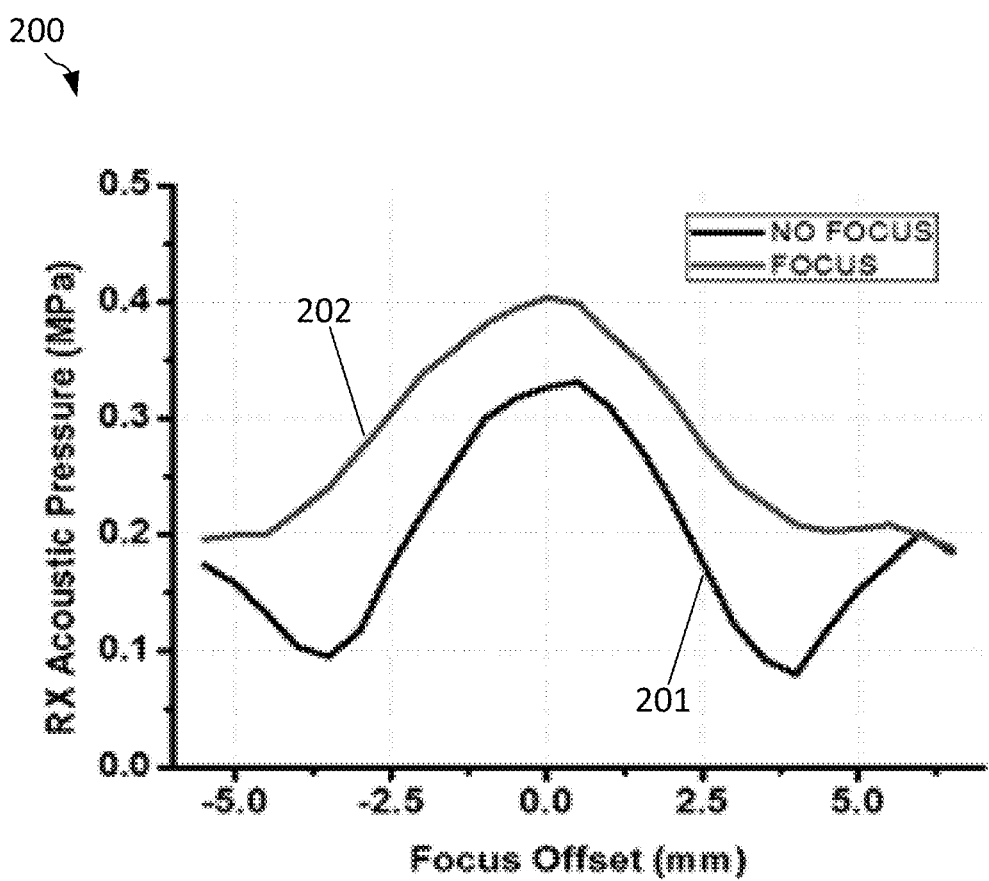
FIG. 2 is a graph generally illustrating performance of a beamformer sequencer with adaptive focusing enabled in accordance with an embodiment of the present disclosure.

FIG. 2 is a graph illustrating performance of an ultrasonic imaging system configured in accordance with aspects of the present disclosure. In particular, the graph includes a focus value offset value (in millimeters) relative to a focus of the phased-array, e.g., of ultrasonic transducer channels 2 along an X axis and a RX acoustic pressure (MPa) value along the Y axis. As shown, the plot 201 shows performance of the system 1 in an unfocused mode when imaging a tank consisting of mineral oil. Notably, mineral oil has similar acoustic properties to that of biomaterial. In the unfocused mode, the beamformer sequencer 36 does not introduce delays of the pulses passed to the AFE 12 by way of delay lines 45. Other approaches to ultrasonic imaging operate exclusively in an unfocused mode, with the beam-focusing and beam-steering being performed off-chip, i.e., within software.

In contrast, the present disclosure may feature beam focusing/forming performed on-chip, for all the array sizes and environment. The beamformer sequencer 36/36A may utilize the aforementioned operational parameters associated with a selected medium to calculate a fractional delay for each ultrasonic transducer channel. In some cases, the beamformer sequencer 36/36A has a time resolution of ~20 ns (which is equal to about 60 microns within water). Plot 202 illustrates performance when the fractional delays are introduced by the beamformer sequencer 36/36A after the parameter uploader utilizes the delay LUT to lookup delay values associated with the target medium. As shown, plot 202 includes a peak RX acoustic pressure value at the center of the focus, i.e., focus offset 0.0, after introduction of such delays. The peak power of plot 202 is significantly larger (e.g., about 25%) than that of the corresponding peak RX acoustic value without introduction of delays.

For portable ultrasound imaging applications in various mediums, the reduction of the power together with a small area is of crucial. In accordance with an embodiment, the proposed TX path 14 only occupies 300×200 μm per channel, which leaves room for vertical integration of IC and ultrasonic transducer elements, where each IC channel corresponds to each ultrasonic transducer channel. For higher frequency scans, the resolution is typically higher, but at the cost of weaker acoustic power. To adapt to these various cases, the system 1 according to one embodiment of the present disclosure may adapt the number of TX drivers per load, depending on both medium attenuation and distance of scan. For example, the system 1 may achieve a drive strength of up to 500 pF per channel at 5 MHz when using a 1:1 relationship between TX driver and transducer channel, or 10 nF at 250 kHz when driving a given channel with TX drivers (e.g., in a 4:1 relationship). Note, in such cases a symmetrical drive signal may be supplied to N number of TX drivers to cause the same to simultaneously drive a given channel.

In an embodiment, the aberration compensation circuit 38 of the DBE 18 may correct phase inequalities related to the unsymmetrical array geometry of the ultrasonic transducer channels 2 and/or lack of uniformity in velocity distribution in a test volume.

An aberration compensation routine of the aberration compensation circuit 38 may be based on, at least in part, the scatter-independent nature of aberration, which means all aberration source can be approximated into the layer close to the surface of the ultrasonic transducer array 2. Aberration compensation circuit 38 may track amplitude maximum of the incoming data and shift TX beamformer delay values accordingly. On the other hand, non-scattering aberration is frequency independent, which simplifies the algorithm, since it does not require spectral filtering. The RX signal on each element can be described as:

$$RX(\alpha,\omega)=s(\alpha;\omega)*f(\alpha;\omega) \quad \text{Equation (1)}$$

Where (A)a is the array element (with the respect to the central point), ω is the phase of the phase of the signal. The f is the integral of the scatters, which can be derived from transmitted signal and transfer function of the media. The aberration correction unit has a transfer function can be represented as:

$$cor(\alpha,\omega)=A(\alpha)e^{i\omega\tau(\alpha)} \quad \text{Equation (2)}$$

Where $A(a)$ is amplitude correction of each element, and τ is the fractional delay of each element and reflects the phase of transmitted signal.

Figure 4A:
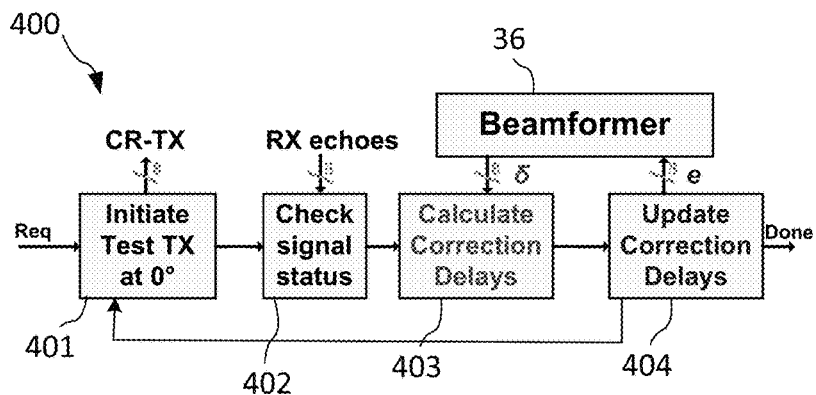
FIG. 4A shows an example process flow for an aberration compensation routine in accordance with an embodiment of the present disclosure.

FIG. 4A shows one example process flow 400 for aberration compensation consistent with an embodiment of the present disclosure. In operation 401, a plurality of test TX signals are sent simultaneously at first instance in time (T=0) to each of the CR-TX pulser circuits to cause a plurality of ultrasonic TX signals to emit (e.g., without introducing delays, thus resulting in a 0 degree directionality for the emitted beam). Note, each of the plurality of ultrasonic TX signals may include N number of pulses.

In operation 402, a plurality of RX echoes are received via the RX path 16, for example. The RX signal for each ultrasonic transducer element can be described using Equation (1) discussed above. In theory, perfectly symmetrical array geometry (e.g., with uniform elements, and element spacing) and a uniform medium (e.g., having uniform velocity of sound throughout) would result in each of the plurality of RX echoes being received at the exact same instance of time, i.e., T+1. However, in reality there may always been some amount of expected variation between arrival times for each of the RX echoes. Differences exceeding a predefined threshold may be indicative of unsymmetrical ultrasonic channel configurations resulting from, for example, defects in manufacturing, component age, contaminates penetrating a device implementing the system 1 (e.g., dust and debris) and so on. Thus, the system 1 may select one or more ultrasonic transducer channels as a reference ($CH_{ref}$) and store an arrival time for a corresponding RX echo signal in a memory for reference and comparison (See FIG. 4B). Likewise, arrival times of RX echo signals associated with other ultrasonic transducer channels may also be stored in the memory for reference purposes.

Figure 4B:
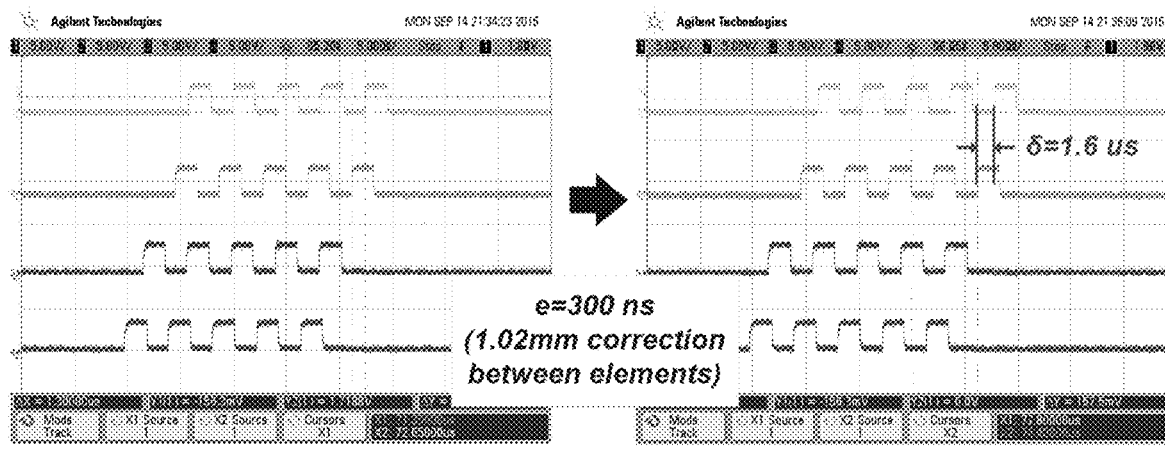
FIG. 4B shows a timing diagram receive (RX) echo pulses for a transmit sequence after performing the aberration compensation routine of FIG. 4A using an aberration compensation circuit consistent with the present disclosure.

As shown in FIG. 4B, the arrival time 410 of CH1 relative to T=0 is 1.3 microseconds. On the other hand, the arrival time 411 of CH2 was 1.6 microseconds relative to T=0. The delta between the arrival time 410 of CH1 and arrival time 411 of CH2 may then be stored in the memory as an error value (e) 412. The error value 412 may then be used to determine a compensated distance 413, with the compensated distance being based on the error value 412 and the speed of sound for the selected medium.

Returning to FIG. 4A, and in operation 403, one or more correction delays may be calculated based on the compensation distance calculated in operation 402. For example, in the previous example of FIG. 4B, CH2 a compensation distance of 1.02 mm was calculated. On the other hand, no compensation was required for CH4 as the arrival time of an associated RX echo signal relative to the arrival time of the RX echo signal was equal, and thus, resulting in an error value of 0.

In operation 404, the beamformer sequencer 36 may then adjust/store a correction delay value for each channel with an associated RX echo signal arrival time that exceeds the predefined threshold. The beamformer sequencer 36 may then utilize the correction delay value associated with a given channel to minimize or otherwise reduce aberration resulting from a mismatch in a ultrasonic transducer channel and/or non-uniformity in a target medium. Operation 404 may include continuing to perform operations 401 to 404 until each ultrasonic transducer channels each have an associated RX echo signal arrival time within the predefined threshold value.

Figure 5:
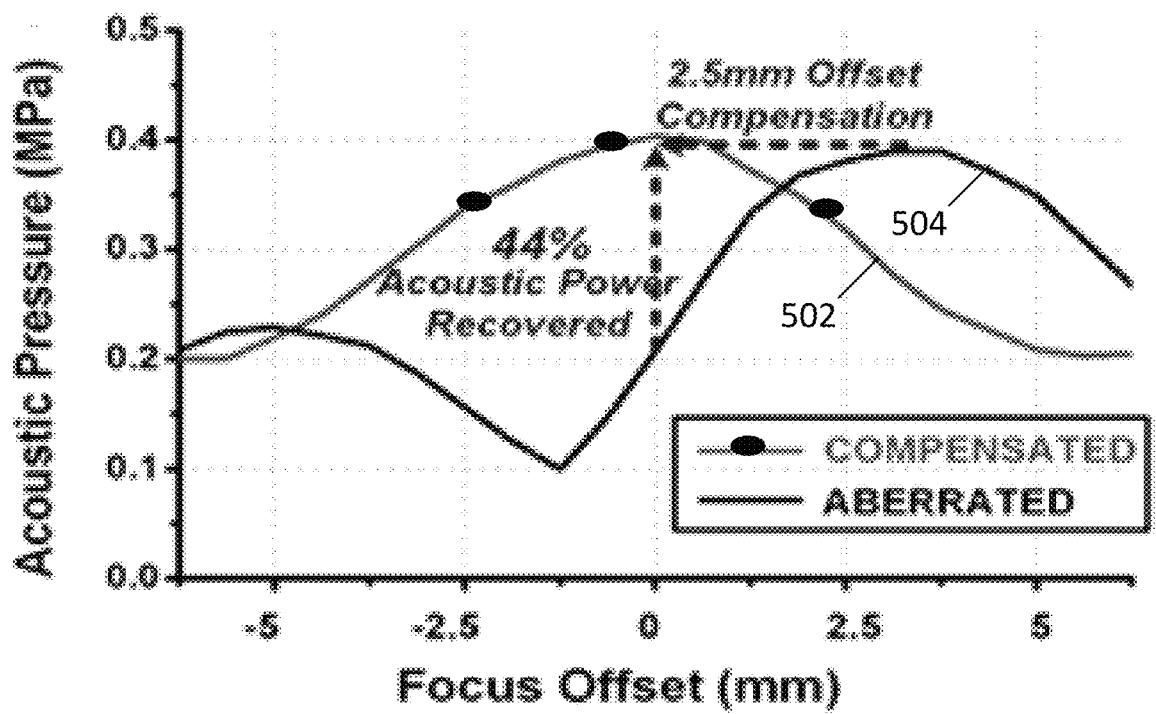
FIG. 5 generally illustrates acoustic wave distribution for an aberrated signal relative to a signal after compensating for aberrations by adjusting one or more pulse delays, in accordance with an embodiment of the present disclosure.

FIG. 5 generally illustrates measured spatial distribution of acoustic pressure in Y-plane generated by 4-ch bimorph pMUT array, and acquired by an ultrasonic transducer consistent with the present disclosure. During normal operation, the peak power should be measured at the focus offset of 0.0 mm relative to the center of the focus of the ultrasonic transducer channels 2. In the event of aberration, the peak power maybe be offset relative to the focus, e.g., as generally illustrated by plot 504. The system 1, and more specifically, the beamformer controller 18 or other suitable controller, may utilize this measured offset to initiate/trigger calibration in accordance with process flow 400 discussed above.

In a simulated error state, e.g., as represented by plot 504 in FIG. 5, a pressure map was acquired at z=15 mm from the surface of a 4-ch pMUT array (see, e.g., FIG. 6C). In this example simulation, channel pitch was 2.3 mm, and each pMUT channel included 180 membranes and a total capacitance of 1.5 nF. The aberrated plot 504 generally represents the measured acoustic pressure distribution at the RX shifted with respect to the intended center of the ultrasonic transducer array due to an incorrect delay introduced to one of the channels (error e=+1 μs for CH1). In an uncompensated state as shown by plot 504, 44% of acoustic power was lost in the test volume and a 2.5 mm offset occurs in the target focal point. This relates to significant loss of the power in the focusing point. After the compensation as generally depicted by plot 502, it can be observed that the acoustic pressure is successfully recovered, and the resulting focused beam at the center of the array (offset=0 mm). As observed, compensation implemented by the aberration circuit 38 recovered 44% of power that would have otherwise been lost.

In high frame rate medical imagers, transmission sequences occur roughly 5× more frequently than in-air rangefinders due to different acoustic speed. Therefore, the total power required to support sufficient acoustic pressure may exceed more than 90% of total system power. The amount of power consumed during imaging is often impacted by the size of the ultrasonic array.

In accordance with an embodiment, a charge redistribution transmit (CR-TX) circuit is disclosed that includes a switching arrangement with a charging mode for driving an ultrasound transducer element with $V_{TX}$ during a charging phase (or driving phase), e.g., based on a pulse-width modulated (PWM) signal, and a redistribution cycle whereby a portion of the charge used to drive the ultrasound transducer element during the driving phase is stored. Advantageously, the stored charge may then be used in combination with $V_{TX}$ during subsequent charging phases, thus significantly reducing the amount of power drawn from the power supply. In some example cases, the amount of charge stored may equal up to 50% of $V_{TX}$, or greater. The resulting overall reduction in power consumption during TX sequences may be 30%, or more, relative to pulser circuits without the CR-TX approach disclosed herein.

Figure 7A:
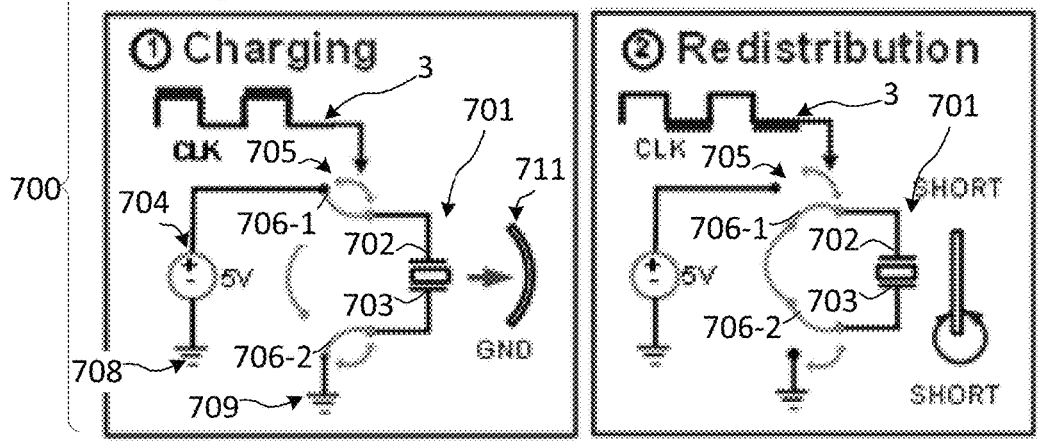
FIGS. 7A-7B generally illustrates one embodiment of a charging redistribution scheme consistent with the present disclosure versus a known charging scheme.
Figure 7B:
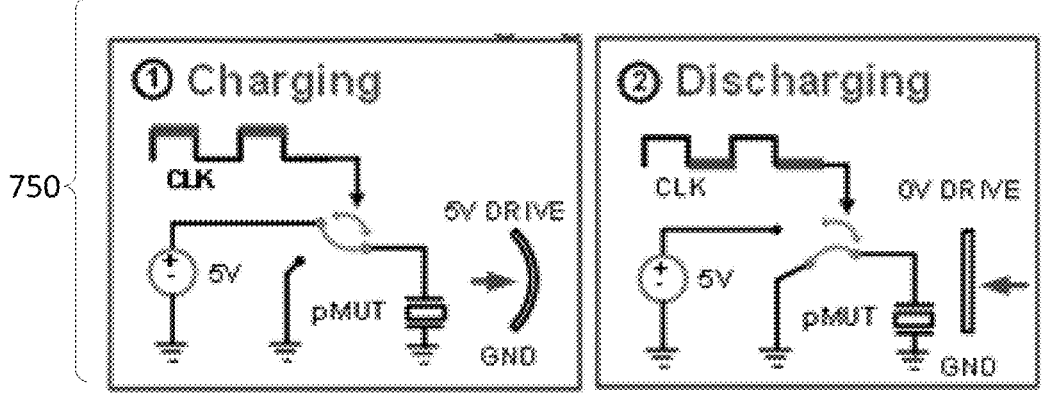

By way of contrast, consider one known approach to a TX driving scheme 750 shown in FIG. 7B. As shown, the ground/bottom electrode of the ultrasonic transducer is electrically coupled to ground, while the driving/top electrode oscillates between ground and driving voltage (or HV shaped pulse). During the charging phase, the ultrasonic transducer device is coupled directly to the power source resulting ΔV over the electrodes equal to $V_{TX}$. During the discharging phase, the driving electrode is electrically coupled to the system ground resulting in ΔV=0. The potential over both electrodes of the ultrasonic transducer is thus equal to the system ground. As a result, each charge gathered on the electrodes is discharged to ground. This results in a total power consumption equal to:

$$P_{TOTAL}=CV^2f \quad \text{Equation (3)}$$

The present disclosure has identified that the total power consumption for a TX circuit may be significantly reduced by utilizing a CR-TX circuit with a switching arrangement to store a portion of the charge gathered on the electrodes that would otherwise be dissipated/wasted. One such example of a CR-TX circuit 700 is shown in FIG. 7A. In an embodiment, a CR-TX circuit consistent with embodiments disclosed herein reduces total power consumption by integrating an on-chip driver with power saving features as variously disclosed herein. In a general sense, a CR-TX circuit aims to re-use at least half of the charge at each driving cycle/phase by electrically decoupling the system ground from the array ground. For the simplicity, the following examples include a bimorph pMUT device represented as a capacitive load with large feedthrough resistance (above 500 kΩ). However, other ultrasonic transducer devices are within the scope of this disclosure.

In an embodiment, the CR-TX circuit 700 may be implemented in each of the CR-TX circuits 14 of FIG. 1. As shown, The CR-TX circuit 700 includes a power supply 704, a switching arrangement 705, a ultrasonic transducer 701, and an array ground 709.

The power supply 704 may output a DC voltage, e.g., 5V, although other output voltages are within the scope of this disclosure. The power supply 704 may comprise one or more batteries, photovoltaic cells, or any combination thereof. The power supply 704 includes a first terminal coupled to system ground 708 and a second terminal coupled to a switching arrangement 705.

The switching arrangement 705 may comprise a first switch 706-1 and a second switch 706-2. The switching arrangement 705 may include circuitry (not shown for simplicity) for receiving the driving signal 3 from the DBE 18. The signal 3 may comprise a pulse-width modulated (PWM) signal. The switching arrangement 705 may then actuate the first and second switches 706-1 and 706-2 to transition between a charging phase (or driving phase) and a redistribution phase based on the driving signal 3. For example, rising edges of each pulse in the driving signal 3 may transition the switching arrangement 705 to a charging phase/mode for a period of time proportional to the width of the pulse. Likewise, the falling edges of each pulse in the signal 3 may then cause the switching arrangement 705 to transition/toggle into a redistribution phase/mode for a period of time proportional to the width of the pulse. The provided example was provided merely for illustration and not intended to be limiting.

As shown in FIG. 7A, the first switch 706-1 of the switching arrangement 705 includes a first end electrically coupled to a driving/top electrode 702 of the ultrasonic transducer 701 and a second end switchably coupled to the power supply 704. The switching arrangement 705 may further a second switch 706-2 with a first end electrically coupled to a ground/bottom electrode 703 of the ultrasonic transducer 701 and a second end switchably coupled to an array ground 709.

In operation, the PWM driving signal 3 is received by the switching arrangement 705. In response to the PWM signal 3 being high (e.g., ON at 5 v or other suitable voltage), the switching arrangement 705 transitions to the charging phase/cycle by electrically coupling the ultrasonic transducer 701 to the power supply 704 and the array ground 709 to generate mechanical energy, e.g., sound 710. During the driving phase, the driving electrode 702 may be charged to $V_{TX}$ while the ground electrode 703 is electrically coupled to the array ground 709, as generally shown in FIG. 7A.

On the other hand, in response to the PWM signal being low (e.g., OFF at 0V or other suitable voltage), switching arrangement 705 transitions to the redistribution phase/cycle by decoupling the driving electrode 702 and ground electrode 703 from the power supply 704 and array ground 709, respectively. As a result, the driving electrode 702 and the ground electrode 703 may be floated momentarily and then electrically coupled with each other to electrically short the driving and ground electrodes 702, 703 together. With an equal electrode size and negligible leakage, the charge redistributes quickly to result in the both electrodes close to but less than $V_{TX}$. For example, the charge may redistribute at $V_{TX}/2$ relative to the system ground 708, although other charge levels may be achieved.

However, since the electrodes of the ultrasonic transducer 701 are shorted with each other, the voltage difference ΔV between the driving and ground electrodes 702, 703 is equal to zero. No voltage over the piezoelectric layer results relaxation of the material and the membrane by itself return to its initial position due to structural resilience (e.g., as generally illustrated in FIG. 6A).

By way of analogy, a pressed spring will return to its original length when applied force is removed. The same holds true after the voltage difference ΔV of the driving and ground electrodes 702, 703 drops to zero. The CR-TX circuit 700 of the present disclosure exploits this phenomenon. During the next charging cycle, each electrode charges in part based on the stored charge instead of charging up from ground to $V_{TX}$, e.g., via a full $V_{TX}$ swing. In instances where the $V_{TX}$ charge is $V_{TX}/2$, then half of the initial charge from the load capacitance is recycled/reused in the next charging cycle, and half the time is needed to charge a given transducer.

Note, the voltage difference ΔV between the driving and ground electrodes 702, 703 is equal to $V_{TX}$. Thus, the total charge required to actuate the membrane in both of the driving scheme of FIGS. 7A and 7B is equal. However, the CR-TX 700 of the present disclosure reuses charges from a previous cycle while maintaining an acoustic performance similar to approaches without a charge reuse scheme. Note that the larger the load, the more power TX circuits will consume. In an embodiment, the total power dissipated for the CR-TX circuit 700 is given by:

$$P_{TOTAL} = \frac{1}{2}CV^2 f \quad \text{Equation (4)}$$

Figure 8:
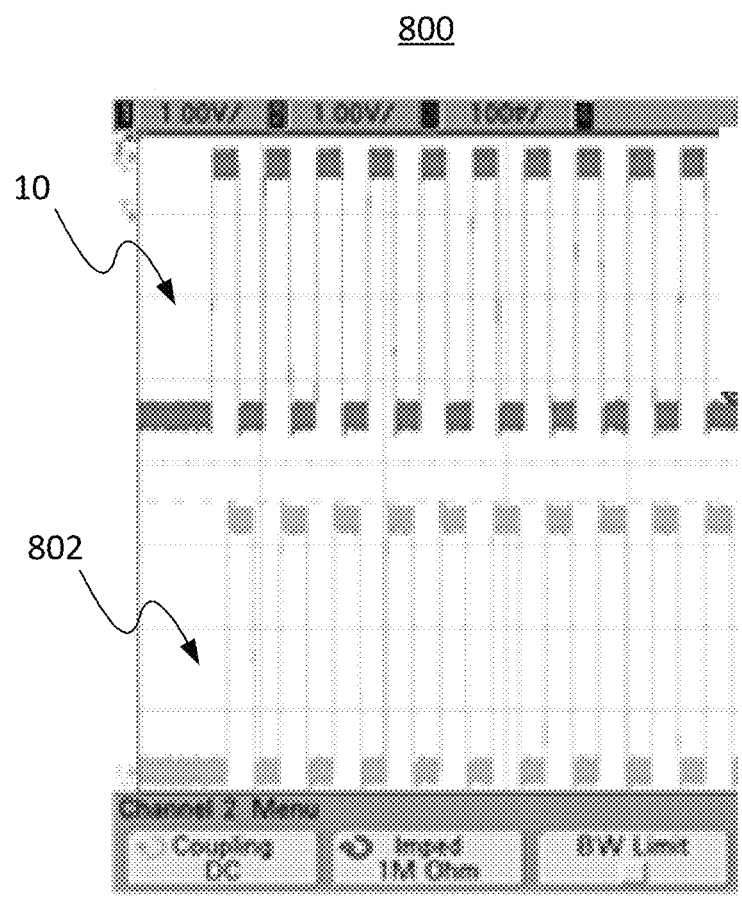
FIG. 8 generally illustrates one embodiment of the charge redistribution performance of the present disclosure compared with a known charging scheme while driving a 100 pF pMUT load.

The measurement of one embodiment of a CR-TX 14 driving a 500 pF pMUT in 1 MHz frequency is presented in the FIG. 8. The graph 800 presents the voltage on both driving and ground electrodes and the relative voltage on a pMUT plates. In this example, the CR-TX 700 is capable of driving very large capacitors (500 pF at 5 MHz or 25 nF at 100 kHz). Reducing the total swing on each driving electrode from $V_{TX}$ to approximately $V_{TX}/2$ (or less) which additionally results in faster charging.

In some embodiments, it may be advantageous for CR-TX 70 to electrically separate system ground 708 with the array ground 709. For example, in the case of multi-channel operation, each element may have two separate electrodes to provide sufficient phase delays. Standard silicon pMUT fabrication process, for example, utilize a bottom electrode as a common ground node and requires only a single driving electrode drive for each element. Bimorph pMUT electrodes, in contrast, include a ground electrode connected together and additional two driving electrodes that allow differential drive of the transducer. Aspects and embodiments disclosed herein are applicable to a wide range of ultrasonic transducers and the examples provided above are not intended to the be limiting.

According to one embodiment, the TX path circuitry 14 (see FIG. 1) occupies 300×200 μm per channel and consumes only 1% of total charging power of 500 pF pMUT at 5 MHz. This power is dissipated in an electrode control logic comprising HV switches (e.g., as generally illustrated in FIG. 7 as switches 706-1 and 706-2). The TX path circuitry 14 configured with a CR-TX scheme as variously disclosed herein produces a similar acoustic performance to that of other known driving schemes (e.g., scheme 750 of FIG. 7B), while total measured power reduction of 32.8% or greater is achieved.

FIG. 3 shows a table that generally compares the performance of the system 1 consistent with the present disclosure with four other systems (e.g., systems 1-4) including ultrasonic transducers. At least one embodiment of a system 1 consistent with the present disclosure consumes 20% lower overall power (both TX and RX combined) than system 2. The TX path circuitry 14 operates in 5× higher acoustic velocities as compared to system 2, since the power performance was measured in mineral oil, not in air. Higher acoustic velocity translates to 10× more frequent TX pulses due to shorter time-of-flight (ToF), which additionally increases the dissipated power.

In an embodiment, an overall area for the system 1 having 8 channels may equal about 700×1490 μm including the power saving CR-TX circuits 14, adaptive digital beamformer 32 with on chip aberration compensation 38, and pulse to echo sequencer 28 with scalable channel numbers.

The system 1 may operate in wide, e.g., 100 kHz-5 MHz bandwidth, and may be capable of driving the phased array of load capacitances up to 500 pF/channel at 5 MHz, and 25 nF/channel at 100 kHz.

The CR-TX circuits 14 reduce the TX power by 30% when compared with 2-voltage system/method 3, while showing the same acoustic performance on 4-ch bimorph pMUT transducer with 180 membranes/channel driven with unipolar 5V. The system 1 may have an overall power in pulse-to-echo mode at 250 kHz and 33% duty cycle driving a 8×500 pF pMUT array at 18.06 mW, where 3.66 mW is consumed by the chip and remaining 80% is delivered to the pMUT array in a power saving CR-TX mode. This translates to the system 1 having an overall energy efficiency of 2.34 μJ/scan for all eight (8) channels including the pMUT array, which is 10% more efficient than system/method 3, while driving 33× larger load, with the same scan depth of 100 mm.

Figure 9:
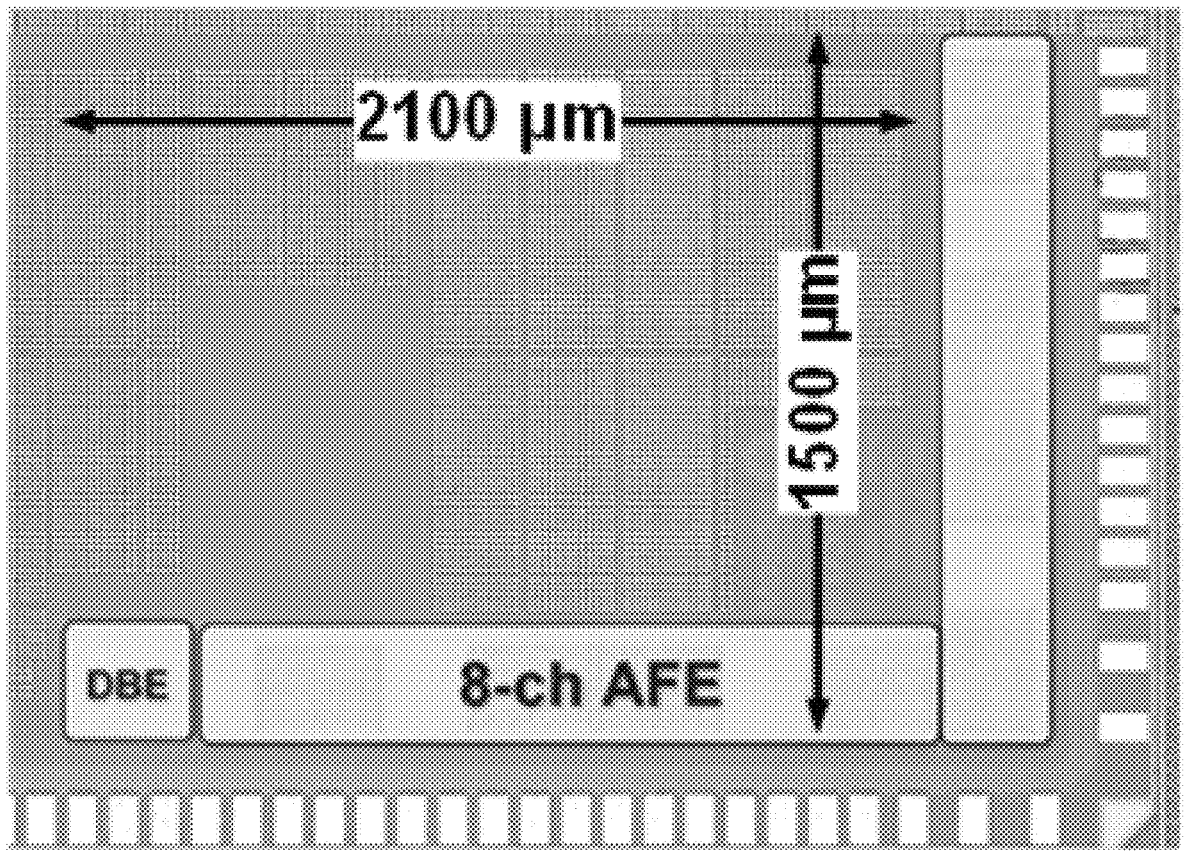
FIG. 9 generally illustrates one embodiment of chip micrograph including a system consistent with the present disclosure.

Turning now to FIG. 9, one embodiment of a chip consistent with the system 1 of the present disclosure fabricated in 65 nm 1P7M CMOS occupies an active area of 700×1490 μm.

Consistent with an aspect of the present disclosure a portable ultrasound system is disclosed. The portable ultrasound system comprising a power supply to output a driving voltage VTX, at least one ultrasonic transducer, each of the at least one ultrasonic transducers having a driving electrode and a ground electrode, and at least one charge redistribution transmit (CR-TX) circuit to receive a driving signal, the at least one transmit circuit comprising a switching arrangement including at least a first switch to transition between a driving phase and a redistribution phase based on the received driving signal and wherein the redistribution phase includes electrically decoupling the at least one ultrasonic transducer from the power supply via the first switch to float the driving electrode and ground electrode of the at least one ultrasonic transducer to cause the at least one ultrasonic transducer to retain a charge based on the first voltage $V_{TX}$.

In accordance with another aspect, a method for driving an ultrasonic transducer is disclosed. The method comprising coupling a driving electrode and a ground electrode of the ultrasonic transducer to a power supply and a ground, respectively, during a first period of time based on a received drive signal, and decoupling the driving electrode and the ground electrode of the ultrasonic transducer from the power supply and the ground, respectively, to float the driving electrode and the ground electrode of the ultrasonic transducer during a second period of time based on the received drive signal to store a charge between the driving electrode to the ground electrode.

In accordance with another aspect, an ultrasound imaging (UIS) system is disclosed. The UIS comprising at least a first and second ultrasound transducer channel, each of the first and second ultrasound transducer channels comprising an array of ultrasound transducers, at least a first and a second transmit (TX) driving circuit, a beamformer controller coupled to the plurality of transmit driving circuits, the beamformer controller to provide a first signal to cause each of the first and second TX driving circuits to electrically couple to the first ultrasound transducer channel and provide a symmetrical driving signal to the first ultrasound transducer channel.

While the principles of the invention have been described herein, it is to be understood by those skilled in the art that this description is made only by way of example and not as a limitation as to the scope of the invention. Other embodiments are contemplated within the scope of the present invention in addition to the exemplary embodiments shown and described herein. Modifications and substitutions by one of ordinary skill in the art are considered to be within the scope of the present invention, which is not to be limited except by the following claims.

What is claimed is:

1. A portable ultrasound system comprising:
   a power supply to output a driving voltage $V_{TX}$;
   an ultrasonic transducer having a driving electrode and a ground electrode; and
   a charge redistribution transmit (CR-TX) circuit to receive a full-swing digital-driving signal to cause the ultrasonic transducer to output ultrasonic sound energy, the CR-TX transmit circuit comprising:
   a switching arrangement including a first switch to transition between a driving phase and a redistribution phase based on the received full-swing digital driving signal and a second switch configured to switchably couple the ground electrode of the ultrasonic transducer to a ground during the driving phase, and to switchably couple the ground electrode to the driving electrode via the first switch during the redistribution phase,
   wherein the driving phase includes electrically coupling the driving electrode to the power supply via the first switch and the ground electrode to the ground via the second switch,
   wherein the redistribution phase includes electrically decoupling the ultrasonic transducer from the power supply via the first switch and decoupling the ground electrode from the ground via the second switch to float the driving electrode and the ground electrode of the ultrasonic transducer to cause the ultrasonic transducer to retain a charge based on the driving voltage $V_{TX}$, and
   wherein the redistribution phase further includes electrically shorting the driving electrode to the ground electrode.

2. The portable ultrasound system of claim 1, wherein the driving phase includes using the retained charge of the ultrasonic transducer during a subsequent driving phase to reduce power consumed from the power supply.

3. The portable ultrasound system of claim 1, wherein the retained charge is equal to about $V_{TX}/2$.

4. The portable ultrasound system of claim 1, wherein the driving phase includes electrically coupling the ultrasonic transducer to the power supply via the first switch to cause the ultrasonic transducer to emit ultrasonic energy.

5. The portable ultrasound system of claim 1, wherein the ground is an array ground.

6. The portable ultrasound system of claim 1, further comprising a system ground associated with the CR-TX circuit and an array ground associated with the ultrasonic transducer.

7. The portable ultrasound system of claim 1, wherein the ultrasonic transducer comprises one of a Piezoelectric Micromachined Ultrasonic Transducer (PMUT), a Capacitive Micromachined ultrasonic transducer (CMUT), or a bulk piezoelectric transducer.

8. The portable ultrasound system of claim 1, wherein the full-swing digital driving signal comprises a pulse-width modulated (PWM) signal.

9. The portable ultrasound system of claim 1, wherein the CR-TX circuit is configured to operate at 100 kHz to 5 MHz based on the received full-swing digital driving signal.

10. The portable ultrasound system of claim 1, wherein the CR-TX circuit is configured generate a drive strength of 500 pF at a rate of 5 MHz based on the received full-swing digital driving signal.

11. The portable ultrasound system of claim 1, comprising a plurality of the CR-TX circuits and wherein each CR-TX circuit in the plurality of the CR-TX circuits is implemented on a same complementary metal oxide semiconductor (CMOS) chip.

12. The portable ultrasound system of claim 1, wherein the power supply comprises at least one of a battery and/or photovoltaic cells.

13. The portable ultrasonic system of claim 1 further comprising:
    wherein the driving phase further includes coupling the driving electrode and the ground electrode of the ultrasonic transducer to the power supply and the ground, respectively, during a first period of time based on the received full-swing digital driving signal; and
    wherein the redistribution phase further includes decoupling the driving electrode and the ground electrode of the ultrasonic transducer from the power supply and the ground, respectively, to float the driving electrode and the ground electrode of the ultrasonic transducer during a second period of time based on the received full-swing digital driving signal to store a charge between the driving electrode to the ground electrode.

14. The portable ultrasound system of claim 13, further comprising shorting the driving electrode and the ground electrode of the ultrasonic transducer subsequent to floating the driving and the ground electrode during the second period of time.

15. The portable ultrasound system of claim 13, wherein the retained charge is equal to or greater than $V_{TX}/4$.

* * * * *